(12) United States Patent
Livinghouse

(10) Patent No.: US 7,078,435 B2
(45) Date of Patent: *Jul. 18, 2006

(54) AUTOINDUCER COMPOUNDS

(75) Inventor: Tom Livinghouse, Bozeman, MT (US)

(73) Assignee: Montana State University, Bozeman, MT (US)

(*) Notice: Subject to any disclaimer, the term of this patent is extended or adjusted under 35 U.S.C. 154(b) by 0 days.

This patent is subject to a terminal disclaimer.

(21) Appl. No.: 10/683,892

(22) Filed: Oct. 10, 2003

(65) Prior Publication Data

US 2004/0254235 A1  Dec. 16, 2004

Related U.S. Application Data

(63) Continuation of application No. 10/099,935, filed on Mar. 13, 2002, now Pat. No. 6,756,404, which is a continuation-in-part of application No. 09/969,501, filed on Oct. 1, 2001, now abandoned, which is a continuation of application No. 09/099,196, filed on Jun. 18, 1998, now Pat. No. 6,337,347.

(51) Int. Cl.
*A01N 43/08* (2006.01)

(52) U.S. Cl. ............... 514/471; 514/473; 514/507; 514/513; 549/321

(58) Field of Classification Search ............... 514/471, 514/473, 507, 513; 549/321
See application file for complete search history.

(56) References Cited

U.S. PATENT DOCUMENTS

| | | | |
|---|---|---|---|
| 4,650,750 A | 3/1987 | Giese | |
| 4,709,016 A | 11/1987 | Giese | |
| 5,239,088 A | 8/1993 | Hoffman et al. | |
| 5,536,750 A | 7/1996 | deSolms et al. | |
| 5,591,872 A * | 1/1997 | Pearson et al. | 549/321 |
| 5,593,827 A | 1/1997 | Bycroft et al. | |
| 5,686,472 A | 11/1997 | Anthony et al. | |
| 6,337,347 B1 * | 1/2002 | Livinghouse | 514/471 |
| 6,756,404 B1 * | 6/2004 | Livinghouse | 514/471 |

FOREIGN PATENT DOCUMENTS

| | | |
|---|---|---|
| JP | 58096079 A | 6/1983 |
| JP | 60045568 A | 3/1985 |
| WO | WO 92/18614 | 10/1992 |
| WO | WO 96/29392 | 9/1996 |
| WO | WO 97/27851 | 8/1997 |
| WO | WO 98/57818 | 12/1998 |

OTHER PUBLICATIONS

Bainton, N.J. et al., "A general role for the *lux* autoinducer in bacterial cell signalling: control of antibiotic biosynthesis in *Erwinia*," *Gene*, 1992, vol. 116, 87-91.

Bainton, N.J. et al., "N-(3-Oxohexanoyl)-L-homoserine lactose regulates carbapenem antibiotic production in *Erwinia carotovora*," *Biochemistry Journal*, 1992, vol. 288, 997-1004.

Bever, R.A. et al., "Molecular Characterization and Nucleotide Sequence of the *Pseudomas aeruginosa* Elastase Structural Gene," *Journal of Bacteriology*, 1988, vol. 170, No. 9, 4309-4314.

Cao, J-G. et al., "Biosynthesis and Stereochemistry of the Autoinducer Controlling Luminescence in *Vibrio harveyi*," *Journal of Bacteriology*, 1993, vol. 175, No. 12, 3856-3862.

Cao, J-G. et al., "Purification and Structural Identification of an Autoinducer for the Luminescence System of *Vibrio harveyi*," *Journal of Biological Chemistry*, 1989, vol. 264, No. 36, 21670-21676.

Choi, S.H. et al., "Genetic Dissection of DNA Binding and Luminescence Gene Activation by the *Vibrio fischeri* LuxR Protein," *Journal of Bacteriology*, 1992, vol. 174, No. 12, 4064-4069.

Eberhard, A. et al., "Analogs of the autoinducer of bioluminescence in *Vibrio fischeri*," *Archives of Microbiology*, 1986, vol. 146, No. 35, 35-40.

Eberhard, A. et al., "Structural Identification of Autoinducer of *Photobacterium fischeri* Luciferase," *Biochemistry*, 1981, vol. 20, 2444-2449.

Eberhard, A. et al., "Synthesis of the *lux* gene autoinducer in *Vibrio fischeri* is positively autoregulated," *Archives of Microbiology*, 1991, vol. 155, 294-297.

Gambello, M.J. and Iglewski, "Cloning and Characterization of the *Pseudomonas aeruginosa lasR* Gene, a Transcriptional Activator of Elastase Expression," *Journal of Bacteriology*, 1991, vol. 173, No. 9, 3000-3009.

Goswami, A. et al., "Microbial Hydroxylation of Quadrone to 8a-Hydroxyquadrone," *Journal of Natural Products*, 1987, vol. 50, No. 1, 49-54.

Hoiby, N. "*Pseudomonas aeruginosa* Infection in Cystic Fibrosis," *Acta. Path. Microbiol. Scand. Sect. B.*, 1974, vol. 82, 551-558.

Iglewski, B.H. and Kabat, D. "NAD-Dependent Inhibition of Protein Synthesis by *Pseudomonas aeruginosa* Toxin," *PNAS USA* 1975, vol. 72, 2284-2288.

Iglewski, B.H. et al., "*Pseudomonas aeruginosa* exoenzyme S: An adenosine diphosphate ribosyltransferase distinct from toxin A," *PNAS USA* 1978, vol. 75, No. 7, 3211-3215.

Jones, S. et al., "The *lux* autoinducer regulates the production of exoenzyme virulence in *Erwinia carotovora* and *Pseudomonas aeruginosa*," *EMBO Journal*, 1993, vol. 12, No. 6, 2477-2482.

(Continued)

Primary Examiner—James Ketter
(74) Attorney, Agent, or Firm—Lahive & Cockfield, LLP; Elizabeth A. Hanley; Maria Laccotripe Zacharakis

(57) ABSTRACT

Autoinducer compounds which enhance gene expression in a wide variety of microorganisms, therapeutic compositions and therapeutic methods wherein gene expression within microorganisms is regulated are disclosed.

24 Claims, No Drawings

OTHER PUBLICATIONS

Kaplan, H.B. and Greenberg, E.P. "Diffusion of Autoinducer Is Involved in Regulation of the *Vibrio fischeri* Luminescence System," *Journal of Bacteriology*, 1985, vol. 163, 1210-1214.

Kessler, E. and Safrin, M. "Synthesis, Processing and Transport of *Pseudomonas aeruginosa* Elastase," *Journal of Bacteriology*, 1988, vol. 170, No. 11, 5241-5247.

Meighen, E.A. "Molecular Biology of Bacterial Bioluminescence," *Microbiological Reviews*, 1991, vol. 55, No. 1, 123-142.

Nicas T.I. and Iglewski, B.H. "The Contribution of exoproducts to virulence of *Pseudomonas aeruginosa*," *Canadian Journal of Microbiology*, 1985, vol. 31, No. 4, 387-392.

Passador, L. et al., "Expression of *Pseudomas aeruginosa* Virulence Genes Requires Cell-to-Cell Communication," *Science*, 1993, vol. 260, 1127-1130.

Pearson, J.P. et al., "Structure of the autoinducer required for expression of *Pseudomonas aeruginosa* virulence genes," *PNAS USA*, 1994, vol. 91, No. 1, 197-201.

Piper, K.R. et al., "Conjugation factor of *Agrobacterium tumefaciens* regulates Ti plasmid transfer by autoinduction," *Nature*, 1993, vol. 362, 448-450.

Pirhonen, M. et al., "A small diffusible signal molecule is responsible for the global control of virulence and exoenzyme production in the plant pathogen *Erwinia carotovora*," *EMBO Journal*, 1993, vol. 12, No. 6, 2467-2476.

Ralling, G. et al., "Growth rate-dependent regulation of RNA polymerase synthesis in *Escherichia coli*," *Mol. Gen. Genet.*, 1985, vol. 201, 379-386.

Reynolds, H.Y. et al., "*Pseudomonas aeruginosa* Infections: Persisting Problems and Current Research to Find New Therapies," *Annals of Internal Medicine*, 1975, vol. 82, No. 6, 819-831.

Stewart, G.S.A.B. and Williams, P., "Shedding New Light On Food Microbiology," *ASM News*, 1993, vol. 59, No. 5, 241-247.

Wierenga, W. and Skulnick, H.I. "General, Efficient, One-Step Synthesis of β-Keto Esters," *Journal of Organic Chemistry*, 1979, vol. 44, No. 2, 310-311.

Williams, P. et al., "Small molecule-mediated density-dependent control of gene expression in prokaryotes: Bioluminescence and the biosynthesis of carbapenem antibiotics," *FEMS Microbiology*, 1992, vol. 100, 161-168.

Zhang, L. et al., "*Agrobacterium* conjugation and gene regulation by N-acyl-L-homoserine lactones," *Nature*, 1993, vol. 362, 446-448.

Passador et al. "Functional Analysis of the *Pseudomonas aeruginosa* Autoinducer PAI" *J. Bacteriol.* 178(20):5995-6000 (1996).

Robson et al. "Bacterial N-acyl-homoserine-lactone-dependent signaling and its potential biotechnological applications" *Trends in Biotechnology* 15:458-64 (1997).

Database Medline Express, US National Library of Medicine, (Bethesda, MD, USA) No. 9730387, C. Reimann et al. "The Global Activator GacA of *Pseudomonas aeruginosa* PAO Postigibely Controls the Production of the Autoinducer N-butryl-homoserine Lactone and the Formation of the Virulence Factors Pyocyanin, Cyanide, and Lipase" abstract, *Molecular Microbiology*, 24(2):309-19 (1997).

Kline, T, et al. "Novel Synthetic Analogs of the Paeudomonas Autoinducer" *Bioorg. Med. Chem. Lett.*, 9(24): 3447-3452 (1999).

Supplementary European Search Report for EP 03 71 4161, 4 pages.

* cited by examiner

AUTOINDUCER COMPOUNDS

RELATED APPLICATIONS

This application is a continuation of U.S. Ser. No. 10/099,935, filed Mar. 13, 2002, now U.S. Pat. No. 6,756,404 which is continuation-in-part of U.S. Ser. No. 09/969,501, filed Oct. 1, 2001, entitled Autoinducer Compounds, now abandoned, which is a continuation of U.S. Ser. No. 09/099,196, filed Jun. 18, 1998, entitled Autoinducer Compounds, issued as U.S. Pat. No. 6,337,347B1. The aforementioned applications and patent are expressly incorporated herein in their entireties by reference.

GOVERNMENT SUPPORT

This work was supported by the National Science Foundation (EEC-8907039). The Government has certain rights in the invention.

TECHNICAL FIELD

The present invention relates to autoinducer compounds which enhance gene expression in a wide variety of microorganisms. The present invention further relates to therapeutic compositions and therapeutic methods wherein, for example, gene expression within microorganisms is regulated.

BACKGROUND ART

Before 1981, microbiologists generally assumed that bacteria lacked the requirement and the capability of producing cell-cell signaling molecules. In 1981, by Eberhard, et al. Biochemistry, 20, 2444–2499, 1981, showed that the bacterium *Photobacterium fischeri* produces a compound 3-oxo-N-(tetrahydro-2-oxo-3-furanyl) hexanamide, also known as vibrio (photobacterium) autoinducer (VAI), which is associated with bacterial luminescence under conditions of high cell density. The cell membrane of *P. fischeri* was shown to be permeable to VAI by Kaplan and Greenberg in 1985 (J. Bacteriol., 163, 1210–1214, 1985). At low bacterial cell densities in broth medium, VAI passively diffuses out of the cells along a concentration gradient, where it accumulates in the surrounding medium. At high cell densities, the concentration of VAI outside the cells is equivalent to the concentration of VAI inside the cells. Under such conditions VAI was shown to initiate transcription of luminescence genes. Using such a system, bacteria are able to monitor their own population density and regulate the activity of specific genes at the population level.

For several years it was presumed that the autoinducer involved in bacterial luminescence was unique to the few bacteria that produce light in the marine environment Then, in 1992, the terrestrial bacterium *Erwinia carotovora* was shown to use an autoinducer system to regulate the production of the β-lactam antibiotic carbapenem (Bainton, et al., Biochem J., 288, 297–1004, 1992b). The molecule found to be responsible for autoinduction of carbapenem was shown to be an acylated homoserine lactone (HSL), a member of the same class of molecules responsible for autoinduction in bioluminescence. This finding led to a general search for HSLs in a wide range of bacteria. To affect the search, a bioluminescence sensor system was developed and used to screen for HSL production in the spent supernatant liquids of a number of bacterial cultures. Many different organisms were shown by the screening to produce HSLs. These included: *Pseudomonas aeruginosa*, *Serratia marcescens*, *Erwinia herbicola*, *Citrobacter freundii*, *Enterobacter agglomerans* and *Proteus mirabilis* (Brainton, et al., Gene. 116, 87–91, 1992a; Swift, et al., Mol. Microbiol., 10, 511–520, 1993). More recently, the list has grown to include *Erwinia stewartii* (Beck, J. Bacteriol, 177, 5000–5008, 1993), *Yersinia enterocolitica* (Throup, et al., Mol. Microbiol., 17, 345–356, 1995), *Agrobacterium tumefaciens* (Zhang, et al., Nature, 362, 446–448, 1993), *Chromobacterium violaceum* (Winston, et al., Proc. Natl. Acad. Sci., USA, 92, 9427–9431, 1995), *Rhizobium leguminosarium* (Schripsema, et al., J. Bacteriol, 178, 366–371 1996) and others. Today it is generally assumed that all enteric bacteria, and the gram negative bacteria generally, are capable of cell density regulation using HSL autoinducers.

In 1993 Gambello, et al. Infect. Immun., 61, 1880–1184, (1993) showed that the α-HSL product of the LasI gene of *Pseudomonas aeruginosa* controls the production of exotoxin A, and of other virulence factors, in a cell density dependent manner. Since that time, the production of a large number of *Pseudomonas* virulence factors have been shown to be controlled by α-HSL compounds produced by the LasI and RhlI regulatory systems (Ochsner, et al., Proc. Natl. Acad. Sci., USA 92, 6424–6428, 1995; Winson, et al., supra; Latifi, et al., 1995), in a manner reminiscent of the Lux system. Latifi, et al. Mol. Microbiol, 21, 1173–1146, (1996) have also shown that many stationary phase properties of *P. aeruginosa*, including those controlled by the stationary phase sigma factor (RpoS), are under the hierarchical control of the LasI and RhlI cell-cell signaling systems.

In all cases, homoserine lactone autoinducers are known to bind to a DNA binding protein homologous to LuxR in *Photobacterium fischeri*, causing a conformational change in the protein initiating transcriptional activation. This process couples the expression of specific genes to bacterial cell density (Latifi, et al. supra, 1996). Regulation of this type has been called 'quorum sensing' because it suggests the requirement for a 'quorate' population of bacterial cells before activation of the target genes (Fuqua, et al., J. Bacteriol., 176, 269–275, 1994b). Expression of certain of these 'virulence factors' has been correlated with bacterial cell density (Finley and Falkow, Microbiol. Rev. 53, 210–230, 1989).

In *P. aeruginosa*, quorum sensing has been shown to be involved in the regulation of a large number of exoproducts including elastase, alkaline protease, LasA protease, hemolysin, cyanide, pyocyanin and rhamnolipid (Gambello, et al., supra; Latifi, et al., supra; Winson, et al., supra; Ochsner, et al., 1995). Most of these exoproducts are synthesized and exported maximally as *P. aeruginosa* enters stationary phase.

The concept of cell signaling and quorum sensing has been studied in the art See for example U.S. Pat. No. 5,591,872, to Pearson et al.; Passador et al., Journal of Bacteriology, pages 5990–6000, October, 1996; PCT W092/18614 and U.S. Pat. No. 5,593,827.

Given the importance of these signaling molecules in the regulation of diverse metabolic functions, there exists a need for new autoinducer compounds which regulate gene expression in bacteria.

DISCLOSURE OF THE INVENTION

An object of the present invention is to provide novel autoinducer compounds and compositions comprising said novel compounds.

A further object of the invention is to provide novel methods for regulation, i.e., inhibition, enhancement, dispersion, etc., by administration of the compounds of the present invention.

Additional objects and advantages of the present invention will be set forth in part in the description which follows and in part will become apparent to those having ordinary skill in the art upon examination of the following or may be learned from the practice of the invention The objects and advantages of the invention may be realized and obtained as particularly pointed out in the appended claims.

According to the present invention, the foregoing and other objects are achieved in part by compounds of the following formulae:

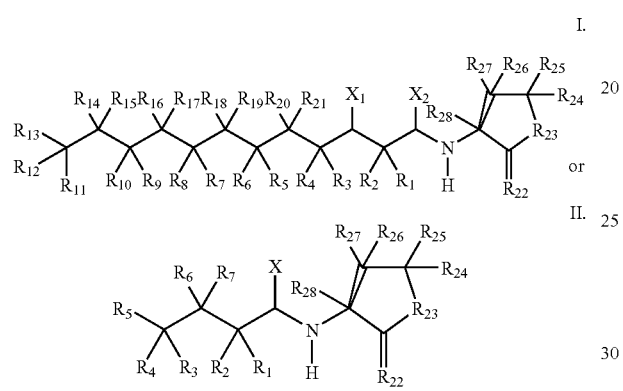

wherein $R_1$–$R_2$, are selected from the group consisting of H, $C_1$–$C_4$ alkyl group, OH, $NH_2$, SH or a halogen, wherein the halogen is selected from the group consisting of fluorine, chlorine, bromine, and iodine;

$R_{22}$ and $R_{23}$ are selected from H, S, O, and N—Y,

Y is selected from H, $C_1$–$C_4$ alkyl group, OH, $NH_2$, SH or a halogen, wherein the halogen is selected from the group consisting of fluorine, chlorine, bromine, and iodine, $R_{24}$–$R_{28}$ is H or a halogen, and X, $X_1$ and $X_2$ are selected from O, S, NH, $H_2$, H plus OH or $NH_2$, or any combination of H plus one halogen or two halogens when one or more R groups is substituted, and at least one of $R_1$–$R_{21}$ is halogen, or the alkylene chain of the molecule contains a sulfur in the chain.

A further object of the present invention is to provide methods for regulating gene expression with a microorganism, which method comprises adding an inventive compound to a microorganism culture to cause expressing of a selected gene that would not otherwise be expressed.

Additional objects and advantages of the present invention will become readily apparent to those having ordinary skill in this art from the following detailed description, wherein only the preferred embodiment of the invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

DESCRIPTION OF THE INVENTION

The present invention relates to autoinducer compounds of the formulae:

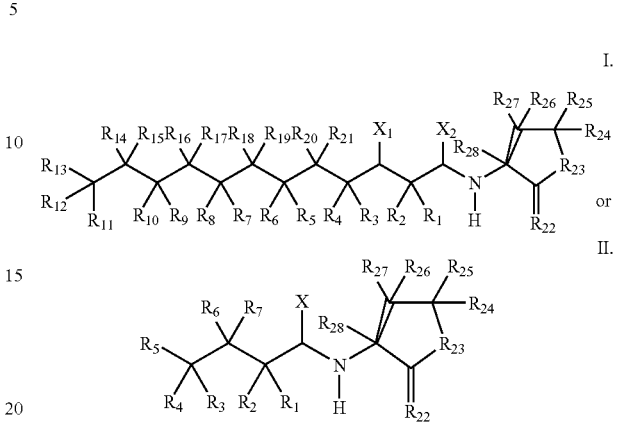

wherein $R_1$–$R_{21}$ are selected from the group consisting of H, $C_1$–$C_4$ alkyl group, OH, $NH_2$, SH or a halogen, wherein the halogen is selected from the group consisting of fluorine, chlorine, bromine, and iodine;

$R_{22}$ and $R_{23}$ are selected from H, S, O, and N—Y,

Y is selected from H, $C_1$–$C_4$ alkyl group, OH, $NH_2$, SH or a halogen, wherein the halogen is selected from the group consisting of fluorine, chlorine, bromine, and iodine, $R_{24}$–$R_{28}$ is H or a halogen, and X, $X_1$ and $X_2$ are selected from O, S, NH, $H_2$, H plus OH or $NH_2$, or any combination of H plus one halogen or two halogens when one or more R groups is substituted, and at least one of $R_1$–$R_{21}$ is halogen, or the alkylene chain of the molecule contains a sulfur in the chain.

Included in the invention are optically active isomers of the claimed compounds as well as analogs of the claimed compounds. The term "isomer" includes molecules having the same molecular formula as the claimed compounds but possessing different chemical and physical properties due to a different arrangement of the atoms in the compound. Isomers include both optical isomers and structural isomers. The phrase "optically active" includes compounds that have the ability to rotate a plane of polarized light. An optically active isomer includes the L-isomer and the D-isomer of the claimed compounds.

The compounds of the present invention encompass compounds of formulae (I) and (II) modified as follows:

1) Alteration of the acyl side chain by increasing or decreasing its length.

2) Alteration of the structure of the acyl side chain, such as addition of a double bond or a triple bond between carbon atoms within the acyl side chain.

3) Substitution on carbons in the acyl side chain, e.g., the addition of a methyl group or other group such as an oxo-group, a hydroxyl group, an amino group, a sulfur atom, a halogen or dihalogen or some other atom or R-group to any location along the acyl side chain.

4) Substitution of carbons comprising the backbone of the acyl side chain with S or S substituted moieties or with N or N substituted moieties.

5) Substitution on the homoserine lactone ring portion of the molecule. For example: addition of a sulfur group to produce a thiolactone.

6) Halogenated acyl furanones have been shown to act as blockers to homoserine lactone cognate receptor proteins.

7) Ring size of the acyl side chain varying heterocyclic moiety is variable. For example, 4-membered and 6-membered rings containing nitrogen (i.e., beta and delta lactams) are included.

The following are specifically preferred compounds of the present invention:

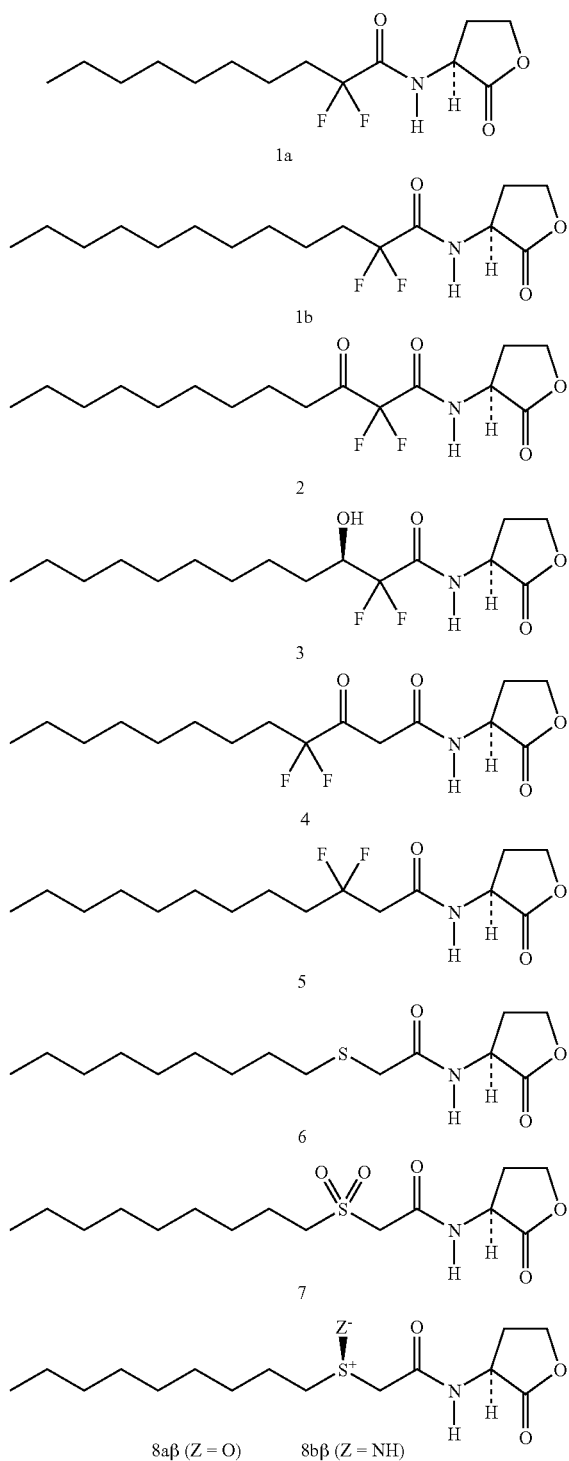

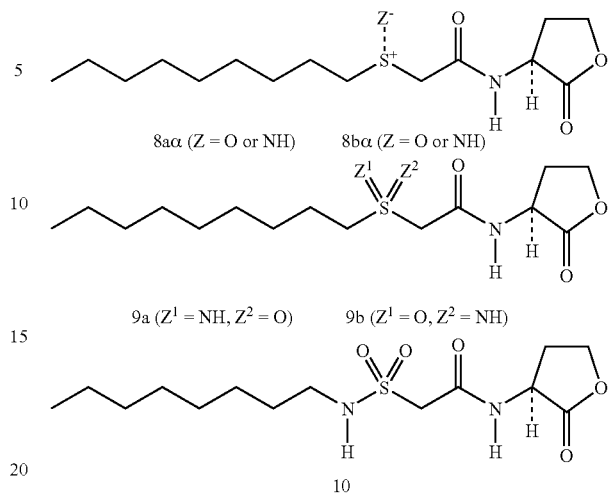

The present invention also relates to a method of regulating the expression of a gene. The method comprises inserting a gene into microorganisms chosen for enhancement of gene expression by an agent capable of stimulating the activity of a selected protein and incubating the microorganism with an agent capable of stimulating the activity of the selected protein. The method further can include the steps of allowing the gene expression to reach a desired level and then incubating the bacteria with an agent capable of inhibiting the activity of the selected protein.

Use is made of these compounds to control gene expression in microorganisms. The control exercised may be to decrease, inhibit, or increase, gene expression. The microorganisms concerned include bacteria, both Gram negative and Gram positive, yeasts and fungi, which have some gene whose expression is affected in some way by at least one of the inventive compounds.

Alternatively, a compound according to the present invention can be added to a microorganism culture in order to cause expression of a particular gene that would not otherwise be expressed. For example, the compound may be used to induce antibiotic production. In yet another example, growth media for microorganisms can be prepared containing an autoinducer compound according to the present invention, at an effective concentration which would lead to a stimulation or promotion of the metabolism, growth and/or recovery of the organisms.

A further method for utilizing the compounds disclosed in the present application is fully disclosed and described in copending U.S. application Ser. No. 09/591,476, filed Jun. 9, 2000, and Ser. No. 09/319,580, filed Jul. 9, 1999.

The present invention further pertains to methods of inhibiting the infectivity of a selected microorganism, methods for treating an immunocompromised host infected by a microorganism, as well as therapeutic compositions. The methods comprise administrating to an individual a therapeutically effective amount of an agent that is capable of inhibiting the activity of a selected protein.

The language "inhibiting the infectivity of a microorganism" means methods of affecting the ability of the microorganism to initially infect or further infect an organism. This includes using agents that prevent a selected protein from activating the transcription of extracellular virulence factors.

The language "agent" means molecules that inhibit the ability of the selected protein to activate transcription of extracellular virulence factors. Inhibitory agents can be selected using method known to those having ordinary skill in the art.

The language "administering a therapeutically effective amount" means methods of giving or applying an agent to an organism which allow the agent to perform its intended therapeutic function. The therapeutically effective amounts of the agent will vary according to factors such as the degree of infection in the individual, the age, sex, and weight of the individual, the ability of the agent to inhibit the activity of the selected protein of the microorganism in the individual. Dosage regimes can be adjusted to provide the optimum therapeutic response. For example, several divided doses can be administered daily or the dose can be proportionally reduced as indicated by the exigencies of the therapeutic situation. Administering also includes contacting the agent with the selected protein outside of an organism such as with a culture of bacteria.

The agent can be administered in a convenient manner such as by injection (subcutaneous, intravenous, etc.), oral administration, inhalation, transdermal application, or rectal administration. Depending on the route of administration, the agent can be coated with a material to protect the agent from the action of enzymes, acids and other natural conditions which may inactivate the agent.

The agent can also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The pro-per fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the agent in the required amount in an appropriate solvent with one or a combination of ingredients enumerated above, as required, followed by filtered sterilization. Generally, dispersions are prepared by incorporating the agent into a sterile vehicle which contains a basic dispersion medium and the required other ingredients enumerated above.

The agent can be orally administered, for example, with an inert diluent or an assimilable edible carrier. The agent and other ingredients can also be enclosed in a hard or soft shell gelatin capsule, compressed into tablets, or incorporated directly into the individual's diet. For oral therapeutic administration, the agent can be incorporated with excipients and used in the form of ingestible tablets, buccal tablets, troches, capsules, elixirs, suspensions, syrups, wafers, and the like. Such compositions and preparations may contain at least about 1% by weight of active component. The percentage of the compositions and preparations can, of course, be varied and can conveniently be between about 5 to about 80% of the weight of the unit. The amount of agent in such therapeutically useful compositions is such that a suitable dosage will be obtained.

The tablets, troches, pills, capsules and the like can also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit For instance, tablets, pills, or capsules can be coated with shellac, sugar or both. A syrup or elixir can contain the agent, sucrose as a sweetening agent, methyl and proplyparabens as preservatives, a dye and flavoring such as cherry or orange flavor. Of course, any material used in preparing any dosage unit form should be pharmaceutically pure and substantially non-toxic in the amounts employed. In addition, the agent can be incorporated into sustained-release preparations and formulations.

The language "pharmaceutically acceptable carrier" means solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the agent, use thereof in the therapeutic compositions and methods of treatment is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the individual to be treated; each unit containing a predetermined quantity of agent is calculated to produce the desired therapeutic effect in association with the required pharmaceutical carrier. The specification for the novel dosage unit forms of the invention are dictated by and directly dependent on (a) the unique characteristics of the agent and the particular therapeutic effect to be achieved, and (b) the limitations inherent in the art of compounding such an agent for the treatment of microbial infection in individuals.

The principal agent is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

The language "an immunocompromised host" means an organism that has an immune system that has impaired capability of reacting to pathogens. The host can be immunocompromised due to a genetic disorder, disease or drugs that inhibit immune response.

The present invention is further illustrated by the following non-limiting examples. The contents of all of the references, published patent applications, and issued patents cited throughout this application are expressly incorporated by reference.

EXAMPLES

Example 1

Chemical Synthesis of Autoinducer Analogs

Synthesis of the fluorinated and sulfur containing analogs of homoserine lactone based autoinducer molecules was achieved by a general condensation procedure involving bis (2-oxo-3-oxazolidinyl) phosphinic chloride (BOP—Cl) mediated union of homoserine lactone with the requisite carboxylic acid similar to that described by Rich, et. al. (Tung, R. D., Rich, D. H. J. Am. Chem. Soc. 1985, 107, 4342–4343). Accordingly, a 0.3 M solution of 2,2-difluoro-3-oxododecanoic acid (vide infra) (1.25 mmol) in $CH_2Cl_2$ was successively treated with (i-Pr)$_2$NEt (1.25 mmol) and BOP—Cl (1.37 mmol). The resulting mixture was vigorously stirred at room temperature for 3 h and then cooled to −78° C. In a separate flask, homoserine lactone.HBr (HSL.HBr) (1.37 mmol) was treated with (i-Pr)$_2$NEt (1.37 mmol) in $CH_2Cl_2$ (1.5 mL) and the mixture stirred at room temperature for 15 min. The resulting solution was added dropwise with stirring over 45 min to the solution containing the mixed BOP-carboxylic acid anhydride at −78° C. The resulting mixture was stirred as it slowly warmed to room temperature over 1.5 h and then stirred at this temperature for an additional 4 h. The reaction mixture was quenched with 1.0 M aq. HCl at 0° C. and the product was extracted with $CH_2Cl_2$. The organic phase was neutralized (NaHCO$_3$ aq.), dried (Na$_2$SO$_4$) and the other solvent was evaporated in vacuo. The crude product was subsequently purified by column chromatography on silica gel (EtOAc for elution) to provide 309 mg (74%) of 2 as a white solid mp 99.3–102.8° C. The autoinducer analogs 1a, 1b, 4, 5, 6, 7 and 10 were synthesized in an analogous manner from HSL.HBr and the corresponding carboxylic acids.

Asymmetric hydrogenation of 2 via the procedure of Noyori, et al. (Matsumura, K.; Hashiguchi, S.; Ikariya, T.; Noyori, R. J. Am. Chem. Soc. 1997, 119, 8738–8739) subsequently furnished the β-hydroxy bearing autoinducer analog 3.

The 2,2-difluoro-3-oxododecanoic acid used in the above preparation was synthesized via the three step sequence outlined below. The method of Freid, et al. (Freid, J. Hallinan, E. A. Tetrahedron Lett. 1984, 25, 2301–2302) was employed to synthesize the corresponding 3-hydroxy ethyl ester. Accordingly, zinc dust (4.40 mmol) in THF (1 ml) was activated by treatment with BrCH$_2$CH$_2$Br (0.13 mmol) at reflux (10 min) followed by Me$_3$SiCl (0.13 mmol) at room temperature (10 min). To the activated zinc was added a solution of decanal (4.00 mmol) and ethyl bromodifluoroacetate (4.40 mmol) in THF (4.0 mL) dropwise over 30 min. The resulting mixture was then stirred for 1 h during which time it was heated briefly to reflux three times. The reaction mixture was then quenched by addition to cold 1.0 N HCl aq. and the product was extracted with EtOAc. The organic phase was successively washed (H$_2$O), dried (brine then MgSO$_4$) and the solvents were removed in vacuo to provide an oil that was purified by column chromatography on silica gel (2% to 5% EtOAc/hexane gradient for elution) to give the aldol product (597 mg, 53%) as a colorless oil.

A solution of (COCl)$_2$ (8.95 mmol) in $CH_2Cl_2$ (20 mL) was cooled to −78° C. and a solution of DMSO (17.80 mmol) in $CH_2Cl_2$ (3.0 mL) was added dropwise over 15 min. The resulting mixture was stirred for an additional 15 min at −78° C. whereupon a solution of the above aldol (3.57 mmol) in $CH_2Cl_2$ (7.0 mL) was added dropwise over 10 min. The mixture was then stirred for 1 h during which time the temperature increased to −40° C. Et$_3$N (5 mL) was then added dropwise over 5 min and the white suspension was allowed to warm to room temperature with stirring. The reaction mixture was added to ice water and the product extracted with $CH_2Cl_2$. The organic phase was successively washed with 1 N (HCl aq., K$_2$CO$_3$ aq., dried (brine then MgSO$_4$), filtered through a plug of silica gel and the solvent was removed in vacuo. The resulting oil was purified by column chromatography on silica gel (1% to 5% EtOAc/hexane gradient for elution) to furnish 850 mg (86%) of the β-ketoester as a colorless oil.

The above β-ketoester (1.72 mmol) in CH$_3$OH (1 mL) was added dropwise to KOH (1.89 mmol) in CH$_3$OH (2 mL) with stirring at 0° C. The resulting mixture was then stirred at room temperature for 24 h, concentrated and the residual CH$_3$OH was removed azeotropically with two portions of C$_6$H$_6$. The resulting white solid was subsequently extracted with two portions of dry hexane and the partitioned between EtOAc (3 ml) and the H$_2$O(5 mL). The resulting mixture was cooled to 0° C. and carefully acidified by the dropwise addition of Conc. HCl aq. (4.0 mL). The mixture was stirred for a further 30 min at 0° C., the layers were separated and the aqueous phase was extracted with EtOAc. The combined organic phases were dried (brine then Mg SO$_4$) and the solvents were evaporated in vacuo to give the β-ketoacid (391 mg, 91%) as a low melting white solid.

The syntheses of the 2,2-difluorocarboxylic acids corresponding to the autoinducer analogs 1a and 1b were performed by the (diethylamino) sulfur trifluoride (DAST) mediated fluorination of the requisite β-ketoesters according to the general procedure of Middleton, et al. (Middleton, W. J.; Bingham, E. M J. org. Chem. 1980, 45, 2883–2887). Accordingly, a solution of methyl 2-oxodecanoate (7.50 mmol) in $CH_2Cl_2$ (10.0 mL) was stirred at 0° C. and DAST (18.70 mmol) was added dropwise over 5 min. The resulting mixture was stirred at 0° C. for 10 min and then at room temperature for 24 h. The reaction mixture was subsequently quenched by slow addition to cracked ice (30 g). After the ice had melted the product was extracted with two portions of $CH_2Cl_2$. The organic phase was dried (brine then Na$_2$SO$_4$) and the solvent was removed in vacuo. The resulting oil was purified by column chromatography on silica gel (2% EtOAc/hexane for elution) to provide the corresponding 2,2-difluoroester (1.43 g, 86%) as a colorless liquid. Saponification of the ester (KOH/methanol, vide supra) provided the corresponding acid after acidification.

The β-ketoacid corresponding to the autoinducer analog 4 was prepared via saponification of the ethyl ester (vide supra) which was synthesized, in turn, by a directed Claisen condensation of methyl 2,2-difluorodecanoate with the lithium enolate of ethyl acetate. Accordingly, EtOAc (1.00 mmol) was added dropwise over 4 min to a stirred solution of (LDA (1.10 mmol) in THF (2.5 mL) maintained at −78° C. The resulting mixture was stirred for a further 30 min at −78° C. whereupon a solution of methyl 2,2-difluorodecanoate (1.00 mmol) in THF (100 μL) was rapidly added. The reaction mixture was subsequently stirred for 2 h at −78° C. and then quenched by the addition of satd. NH₄Cl aq. (1 mL). The resulting mixture was poured into H₂O (5 mL) and the product was extracted with three portions of Et₂O. The combined organic phases were dried (brine then MgSO₄), filtered through a plug of silica gel and the solvent was removed in vacuo. Purification of the product by column chromatography on silica gel (5% to 10% to 40% EtOAc/hexane gradient for elution) provided the requisite β-ketoester (222 mg, 80%) as a clear, faint yellow oil.

3,3-Difluorododecanoic acid (corresponding to the autoinducer analog 5) was prepared by the oxidation of 2,2-difluoro-1-phenylundecane [prepared, in turn, via the fluorination of 1-phenylundecan-2-one with DAST (vide supra)] by the procedure of Sharpless, et al. (Carlsen, P H. J.; Katsuki, T.; Martin, V. S.; Sharpless, K. B. J. Org. Chem. 1981, 46, 3936–3938). Accordingly, a mixture consisting of 2,2-difluoro-1-phenylundecane (1.00 mmol), CCl₄ (2 mL), CH₃CN (2 mL), H₂O(3 mL) and NaIO₄ (14.50 mmol) was vigorously stirred at room temperature and RuCl₃ hydrate (5 mg) was added. The reaction mixture was vigorously stirred for a further 2 h at room temperature and then CH₂Cl₂ (10 mL) was added and the phases were separated. The upper aqueous phase was extracted with three portions of CH₂Cl₂ and the combined organic phases were dried (MgSO₄) and the solvent was removed in vacuo. The crude product was purified by bulb-to-bulb distillation at 0.05 Torr to provide 3,3-difluorododecanoic acid (203 mg, 86%) as a colorless oil.

Synthesis for the sulfur containing autoinducer analogs and their carboxylic acid precursors are described below. (Nonylthio)acetic acid and (nonylsulfonyl)acetic acid (corresponding to the autoinducer analogs 6 and 7 respectively) were synthesized by the general protocol of Davenport, et al. (Kenney, W. J., Walsh J. A., Davenport, D. A. J. Am. Chem. Soc. 1961, 83, 4019–4022). Accordingly, a solution of NaOH (0.21 mol) in H₂O (45 mL) was added dropwise to a stirred solution of nonanethiol (0.10 mol) and chloroacetic acid (0.11 mol) in EtOH (125 mL). The resulting mixture was stirred at reflux for 12 h and the majority of the EtOH was subsequently removed in vacuo. The resulting aqueous phase was acidified with conc. HCl$_{aq}$. and the crude product was extracted with toluene. The organic phase was dried (brine then MgSO₄) and the solvent was evaporated in vacuo to provide an oil that was purified by distillation at 0.05 Torr to provide (17.7 g, 81%) of (nonylthio)acetic acid as a colorless oil. A stirred solution of (nonylthio)acetic acid (25 mmol) in AcOH (50 mL) was cooled in an ice bath and 30% aqueous H₂O₂ (55 mmol) was slowly added in a dropwise fashion. The resulting mixture was subsequently stirred at 0° C. for 5 h and then at room temperature for 12 h. Evaporation of the AcOH and H₂O in vacuo followed by azeotropic removal of the last traces of these solvents with two portions of toluene furnished (nonylsulfonyl)acetic acid in near quantitative yield. Coupling of the above carboxylic acids with HSL.BRr mediated by BOP—Cl in the presence of (i-Pr)₂NEt (vide supra) gave the autoinducer analogs 6 and 7.

The sulfoxide bearing autoinducer analogs 8aα and 8aβ were synthesized by the peracid oxidation of 6. Accordingly, a solution of 6 (1 mmol) in CH₂Cl₂ (8 mL) was stirred at −10° C. and a solution of freshly purified m-chloroperoxybenzoic acid (1 mmol) in CH₂Cl₂ (2 mL) was added dropwise over 5 min. The resulting mixture was subsequently stirred at −10° C. for 1 h and 0° C. for 3 h. The reaction mixture was diluted with Et₂O (50 mL) and extracted with 35% KHCO$_{aq}$. (15 mL). The aqueous layer was then back extracted with EtOAc (2×15 mL). The combined organic phases were dried (MgSO₄) and the solvents were evaporated in vacuo to provide a mixture of the diastereomeric sulfoxides 8aα and 8aβ (279 mg, 88%) that could be separated into the pure stereoisomers by preparative HPLC using a reversed phase (C₁₈) column (CH₃OH/CH₃CN gradient for elution). The sulfoximine bearing autoinducer analogs 9a and 9b were synthesized from the corresponding diastereomeric sulfoxides (e.g. 8aα and 8aβ respectively) following the general procedure for S-amination described by Ikeda, et al. (Tamura, Y., Sumoto, K., Minaminkawa, J., Ikeda, M. Tetrahedron Lett. 1972, 13, 4137–4140). Accordingly, a solution of O-mesitylenesulfonylhydroxylamine (MSH) (0.25 mmol) in CH₂Cl₂ (1 mL) was added dropwise to a stirred solution of sulfoxide 8aβ (0.25 mmol) in CH₂Cl₂ (2.5 mL) at 0° C. The resulting mixture was subsequently stirred at room temperature for 90 min and the solvent was evaporated in vacuo. Ethyl acetate (10 mL) was added to the residue and the resulting mixture was stirred at 0° C. whereupon a solution of N-methylmorpholine (0.25 mmol) in EtOAc (0.5 mL) was added dropwise by syringe. The resulting mixture was stirred at room temperature for 30 min and was then filtered through Florisil (1.5 g) (EtOAc for elution). Evaporation of the solvent in vacuo furnished sulfoximine 9a (76 mg, 91%) which could be further purified by reversed phase (C₁₈) column chromatography.

The sulfilimine bearing autoinducer analogs 8bα and 8bβ were prepared and isolated as a mixture of diastereomers in the form of the corresponding mesitylenesulfonate salts via the S-amination of 6 mediated by MSH (vide supra). Accordingly, a solution of MSH (0.50 mmol) in CH₂Cl₂ (2 mL) was added dropwise to a stirred solution of 6 (0.50 mmol) in CH₂Cl₂ (5 mL) at 0° C. The resulting mixture was subsequently stirred at room temperature for 1 h and the solvent was evaporated in vacuo. Trituration of the residue with Et₂O gave the corresponding sulfiliminium mesitylenesulfonates 8bα and 8bβ (217 mg, 84%) as a diastereomeric mixture.

The synthesis of the sulfonamide containing carboxylic acid precursor corresponding to the autoinducer analog 10 was accomplished by the two step sequence described below. Accordingly, a solution of α-toluenesulfonyl chloride (10 mmol) in CH₂Cl₂ (5 mL) was added dropwise to a stirred solution of octylamine (20 mmol) in CH₂Cl₂ (20 mL) at 0° C. The resulting mixture was subsequently stirred at room temperature for 30 min and was then extracted with H₂O (3×24 mL) The organic phase was dried (MgSO₄) and the solvent was evaporated in vacuo to provide the corresponding α-toluenesulfonamide (262 mg, 93%) as a colorless solid. Subsequent oxidative degradation of the phenyl moiety within this compound via the procedure of Sharpless, et al. [e.g., cat. RuCl₃ hydrate, NaIO₄, H₂O/CH₃CN/CCl₄ (vide supra)] furnished the α-sulfonamidoacetic acid corresponding to homoserine lactone 10. Accordingly, a mixture of the above α-toluenesulfonamide (1.00 mmol), CCl₄ (2 mL), CH₃CN (2 mL), H₂O (3 mL) and NaIO₄ (14.50 mmol) was vigorously stirred at room temperature and RuCl₃ hydrate (5 mg) was added. The reaction mixture was vigorously stirred for a further 2 h at room temperature and then CH₂Cl₂ (10 mL) was added and the phases were separated. The upper aqueous phase was extracted with three portions of CH₂Cl₂ and the combined organic phases were dried (MgSO₄) and the solvents were removed in vacuo. Recrystallization of the residue from EtOH provided the α-sulfonamidoacetic acid (181 mg, 72%) as a colorless solid.

Incorporation by Reference

The contents of all references, patents and published patent applications cited throughout this application are hereby incorporated herein in their entireties by reference.

Equivalents

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A compound of the following formula:

[chemical structure with substituents $R_1$–$R_{28}$, $X_1$, $X_2$]

wherein $R_1$–$R_{21}$ are selected from the group consisting of H, $C_1$–$C_4$ alkyl group, OH, $NH_2$, SH and a halogen, wherein the halogen is selected from the group consisting of fluorine, chlorine, bromine, and iodine;

$R_{22}$ and $R_{23}$ are selected from H, S, O, and N—Y,

Y is selected from H, $C_1$–$C_4$ alkyl group, OH, $NH_2$, SH or a halogen, wherein the halogen is selected from the group consisting of fluorine, chlorine, bromine, and iodine, $R_{24}$–$R_{28}$ is H or a halogen, $X_1$ and $X_2$ are selected from O, S, NH, $H_2$, H plus OH or $NH_2$, or any combination of H plus one halogen or two halogens when one or more R groups is substituted, and at least one of $R_1$–$R_{21}$ is halogen, or the alkylene chain of the molecule contains a sulfur in the chain; and wherein the alkylene chain of the molecule contains a nitrogen in the chain, or the alkylene chain of the molecule contains one or more double bonds or triple bonds between the carbon atoms within the chain, or the homoserine lactone portion of the molecule contains a sulfur in the ring.

2. The compound of claim 1, wherein $R_{24}$ through $R_{28}$ are a H or halogen, and $R_{22}$–$R_{23}$ are a H.

3. The compound of claim 2, wherein one or more carbons forming the backbone of the molecule are substituted with S or S-substituted moieties.

4. The compound of claim 2, wherein the carbonyl group at $X_1$ and/or $X_2$ is substituted with $H_2$, H plus a halogen or two halogens.

5. The compound of claim 1, wherein $R_{22}$ is selected from H, S, O and N—Y, and $R_{23}$ is independently selected from S, O, and N—Y, wherein Y is selected from H, $C_1$–$C_4$ alkyl group, OH, $NH_2$, SH or a halogen, wherein the halogen is selected from the group consisting of fluorine, chlorine, bromine, and iodine.

6. The compound of claim 1, wherein $X_1$–$X_2$ is selected from $H_2$, H plus a halogen, two halogens, H plus OH or $NH_2$, a double bonded O, NH, or S.

7. The compound of claim 1, which is an optically active isomer.

8. A compound of the following formula:

[chemical structure with substituents $R_1$–$R_7$, $R_{22}$–$R_{28}$, X]

wherein $R_1$–$R_7$ are selected from the group consisting of H, $C_1$–$C_4$ alkyl group, OH, $NH_2$, SH or a halogen, wherein the halogen is selected from the group consisting of fluorine, chlorine, bromine, and iodine;

$R_{22}$ and $R_{23}$ are selected from H, S, O, and N—Y,

Y is selected from H, $C_1$–$C_4$ alkyl group, OH, $NH_2$, SH or a halogen, wherein the halogen is selected from the group consisting of fluorine, chlorine, bromine, and iodine, $R_{24}$–$R_{28}$ is H or a halogen, X is selected from O, S, NH, $H_2$, H plus OH or $NH_2$, or any combination of H plus one halogen or two halogens when one or more R groups is substituted, and at least one of $R_1$–$R_7$ is halogen, or the alkylene chain of the molecule contains a sulfur in the chain; and wherein the alkylene chain of the molecule contains a nitrogen in the chain, or the alkylene chain of the molecule contains one or more double bonds or triple bonds between the carbon atoms within the chain, or the homoserine lactone portion of the molecule contains a sulfur in the ring.

9. The compound of claim 8, wherein $R_{22}$ is selected from H, S, O and N—Y, and $R_{23}$ is independently selected from S, O, and N—Y, wherein Y is selected from H, $C_1$–$C_4$ alkyl group, OH, $NH_2$, SH or a halogen, wherein the halogen is selected from the group consisting of fluorine, bromine, and iodine.

10. The compound of claim 8, wherein X is selected from $H_2$, H plus a halogen, two halogens, H plus OH or $NH_2$, a double bonded O, NH or S.

11. The compound of claim 8, which is an optically active isomer.

12. A pharmaceutical composition comprising at least one compound of the following formulae:

I.

[chemical structure I with substituents $R_1$–$R_{28}$, $X_1$, $X_2$]

or

II.

[chemical structure II with substituents $R_1$–$R_7$, $R_{22}$–$R_{28}$, X]

wherein $R_1$–$R_{21}$ are selected from the group consisting of H, $C_1$–$C_4$ alkyl group, OH, $NH_2$, SH or a halogen, wherein the halogen is selected from the group consisting of fluorine, chlorine, bromine, and iodine;

$R_{22}$ and $R_{23}$ are selected from H, S, O, and N—Y,

Y is selected from H, $C_1$–$C_4$ alkyl group, OH, $NH_2$, SH or a halogen, wherein the halogen is selected from the group consisting of fluorine, chlorine, bromine, and iodine, $R_{24}$–$R_{28}$ is H or a halogen, X, $X_1$ and $X_2$ are selected from O, S, NH, $H_2$, H plus OH or $NH_2$, or any combination of H plus one halogen or two halogens when one or more R groups is substituted, and at least one of $R_1$–$R_{21}$ is halogen, or the alkylene chain of the molecule contains a sulfur in the chain; and wherein the alkylene chain of the molecule contains a nitrogen in the chain, or the alkylene chain of the molecule contains one or more double bonds or triple bonds between the carbon atoms within the chain, or the homoserine lactone portion of the molecule contains a sulfur in the ring.

and a pharmaceutically acceptable carrier.

13. The composition of claim 12, wherein the compound is present in an amount effective to affect the ability of a microorganism to initially infect or further infect an organism.

14. The composition of claim 12, further comprising an antimicrobial, antibacterial or antifungal agent.

15. A growth medium for microorganisms comprising a compound of the formula as defined in claim 1 or 8, at a concentration effective to stimulate or promote the metabolism, growth and/or recovery of the microorganisms.

16. A method for regulating gene expression with a microorganism, which method comprises inserting a gene into a microorganism chosen for enhancement of gene expression by a compound of the formula as defined in claim 1 or 8, capable of stimulating the activity of a selected protein and incubating the microorganism with the compound.

17. A method for regulating gene expression comprising adding a compound of the formula as defined in claim 1 or 8, to a microorganism culture to cause expression of a selected gene that would not otherwise be expressed.

18. A method of inhibiting the infectivity of a selected microorganism, comprising contacting the selected microorganism with a compound of the formula as defined in claim 1 or 8.

19. A compound according to claim 1 wherein $R_1$–R21 is $CH_3$.

20. A compound according to claim 8 wherein $R_1$–$R_7$ is $CH_3$.

21. A composition according to claim 12 wherein $R_1$–$R_{21}$ is $CH_3$.

22. A compound according to claim 1 which is an optical isomer.

23. A compound according to claim 8 which is an optical isomer.

24. A composition of claim 12 wherein the compound is an optical isomer.

* * * * *